(12) United States Patent
Kram

(10) Patent No.: US 7,425,306 B1
(45) Date of Patent: Sep. 16, 2008

(54) SLIDE HEATER

(75) Inventor: Brian H. Kram, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 290 days.

(21) Appl. No.: 09/953,417

(22) Filed: Sep. 11, 2001

(51) Int. Cl.
*G01N 25/00* (2006.01)

(52) U.S. Cl. .................................. 422/67; 436/45

(58) Field of Classification Search .......... 422/100, 422/102, 104, 67; 436/43, 45
See application file for complete search history.

(56) References Cited

U.S. PATENT DOCUMENTS

| | | | |
|---|---|---|---|
| 3,977,568 A | 8/1976 | Smith | |
| 3,979,576 A | 9/1976 | Janson | |
| 4,043,292 A | 8/1977 | Rogers et al. | |
| 4,092,952 A | 6/1978 | Wilkie et al. | |
| 4,296,069 A | 10/1981 | Smith et al. | |
| 4,358,470 A | 11/1982 | Rasmussen | |
| 4,384,193 A | 5/1983 | Kledzik et al. | 219/521 |
| 4,430,299 A | 2/1984 | Horne | |
| 4,543,236 A | 9/1985 | von Gise | |
| 4,629,862 A | 12/1986 | Kitagawa et al. | |
| 4,635,791 A | 1/1987 | Jackson et al. | |
| 4,777,020 A | 10/1988 | Brigati | 422/99 |
| 4,798,706 A | 1/1989 | Brigati | 422/102 |
| 4,801,431 A | 1/1989 | Cuomo et al. | 422/104 |
| 4,847,208 A | 7/1989 | Bogen | |
| 4,858,155 A | 8/1989 | Okawa et al. | |
| 4,865,986 A | 9/1989 | Coy et al. | |
| 4,985,206 A | 1/1991 | Bowman et al. | |
| 5,075,079 A | 12/1991 | Kerr et al. | |
| 5,105,066 A | 4/1992 | Houdy et al. | |
| 5,154,889 A | 10/1992 | Muraishi | |
| 5,207,987 A | 5/1993 | Kureshy et al. | |
| 5,280,156 A | 1/1994 | Niori et al. | |
| 5,316,452 A | 5/1994 | Bogen et al. | |
| 5,425,918 A | 6/1995 | Healey et al. | |
| 5,439,649 A | 8/1995 | Tseung et al. | 422/99 |
| 5,496,518 A | 3/1996 | Arai et al. | |
| 5,523,056 A | 6/1996 | Miller | |
| 5,589,649 A | 12/1996 | Brinker et al. | |
| 5,601,141 A | 2/1997 | Gordon et al. | |
| 5,654,200 A | 8/1997 | Copeland et al. | 436/46 |
| RE35,716 E | 1/1998 | Stapleton et al. | 435/3 |
| 5,839,091 A | 11/1998 | Rhett et al. | |

(Continued)

FOREIGN PATENT DOCUMENTS

EP  0 201 780  11/1986

(Continued)

OTHER PUBLICATIONS

Stross, W. et al., J. Clin. Pathol. 42: 106-112 (1989), *Automation of APAAP Immunocytochemical Technique*.

(Continued)

*Primary Examiner*—Lyle A Alexander
(74) *Attorney, Agent, or Firm*—Hayes Soloway P.C.

(57) ABSTRACT

A slide heater for use in a slide processing apparatus in which an interface surface between the slide heater and the slide has a plurality of slots or channels terminating in an edge thereof, for gathering and venting gas bubbles.

18 Claims, 8 Drawing Sheets

U.S. PATENT DOCUMENTS

| | | | |
|---|---|---|---|
| 5,947,167 A | 9/1999 | Bogen et al. | |
| 6,092,695 A | 7/2000 | Loeffler | |
| 6,096,271 A | 8/2000 | Bogen et al. | |
| 6,133,548 A | 10/2000 | Grover et al. | 219/386 |
| 6,180,061 B1 | 1/2001 | Bogen et al. | |
| 6,183,693 B1 | 2/2001 | Bogen et al. | |
| 6,296,809 B1 | 10/2001 | Richards et al. | 422/64 |
| 6,358,473 B1 | 3/2002 | Coello et al. | 422/99 |
| 6,399,394 B1 * | 6/2002 | Dahm et al. | 436/180 |
| 6,495,106 B1 | 12/2002 | Kaira et al. | |
| 6,541,261 B1 | 4/2003 | Bogen et al. | |
| 6,582,962 B1 | 6/2003 | Richards et al. | |
| 6,673,620 B1 | 1/2004 | Leoffler et al. | |
| 6,783,733 B2 | 8/2004 | Bogen et al. | |
| 6,827,900 B2 | 12/2004 | Thiem et al. | |
| 2002/0054830 A1 | 5/2002 | Bogen et al. | |
| 2004/0191128 A1 | 9/2004 | Bogen et al. | |
| 2004/0241050 A1 | 12/2004 | Bogen et al. | |

FOREIGN PATENT DOCUMENTS

| | | |
|---|---|---|
| WO | WO 93/09486 | 5/1993 |
| WO | WO 99/44031 | 9/1999 |
| WO | WO 01/25750 | 4/2001 |

OTHER PUBLICATIONS

Stark, E et al., J. Immunol Methods. 107:89-92 (1988), *An Automated Device for Immunocytochemistry*.

Unger, E., Brigati D, et al. J. Histotechnology 11: 253-258 (1988), *Automation of In situ Hybridization: Application of the Capillary Action Robotic Workstation*.

"Journal of Histotechnology 11(3)" Brigati, 1988, pp. 165-183.

"The Complete Immunoperoxidase System," IMMULOK, advertisement, 1 pg.

United States Cour of Appeals for the Federal Court, *Cytologix Corporation v. Ventana Method Systems, Inc.*, Case No. 04-1446, Deceision decided Sep. 21, 2005, pp. 1-18.

* cited by examiner

SLIDE HEATER

TECHNICAL FIELD

The present invention relates to slide processing apparatus, and more particularly to improvements in heaters for slides for biological reaction analysis slide processing systems.

BACKGROUND ART

Immunostaining and in situ DNA analysis are useful tools in histological diagnosis and the study of tissue morphology. Immunostaining relies on the specific binding affinity of antibodies with epitopes in tissue samples, and the increasing availability of antibodies which bind specifically with unique epitopes present only in certain types of diseased cellular tissue. Immunostaining requiring a series of treatment steps conducted on a tissue section mounted on a glass slide to highlight by selective staining certain morphological indicators of disease states. Typical steps include pretreatment of the tissue section to reduce non-specific binding, antibody treatment and incubation, enzyme labeled secondary antibody treatment and incubation, substrate reaction with the enzyme to produce a fluorophore or chromophore highlighting areas of the tissue section having epitopes binding with the antibody, counterstaining, and the like. Each of these steps is separated by multiple rinse steps to remove unreacted residual reagent from the prior step. Incubations typically are conducted at around 40° C., while cell conditioning steps typically are conducted at somewhat higher temperatures, e.g. 90-100° C. In-situ DNA analysis relies upon the specific binding affinity of probes with unique nucleotide sequences in cell or tissue samples and similarly involves a series of process steps, with a variety of reagents and process temperature requirements.

Automated systems have been proposed to introduce cost savings, uniformity of slide preparation, and reduction of procedural human errors. Stross, W. et al, J. Clin. Pathol. 42: 106-112 (1989) describes a system comprising a series of baths positioned under the circumference of a circular, rotatable disc from which slide trays are suspended. The disc is lifted to lift slide trays from their baths, turned to position the slide trays above the next consecutive bath, and lowered to immerse the slide trays in the baths. This operation can be automated with suitable timers and switches. This system exposes each of the slides to the same treatment and relies on dipping for application of reactants and rinsing.

Stark, E. et al, J. Immunol. Methods. 107: 89-92 (1988) describes a microprocessor controlled system including a revolving table or carousel supporting radially positioned slides. A stepper motor rotates the table, placing each slide under one of the stationary syringes positioned above the slides. A predetermined volume of liquid, determined by a dial, is delivered to a slide from each syringe. Microprocessor controls are provided.

Cosgrove, R. et al, ACL. pp 23-27 (December, 1989) describe an immunostaining apparatus for auto-pipetting reagents into a slide well from a carousel holding up to 18 reagent vials. Below each well, a coverplate spaced from the surface of each slide provides cover and defines a reagent flow channel. The slides are suspended at a steep angle. Reagent from the well flows downward over the slide surface. A row of slides are suspended for sequential treatment. Washing is accomplished by a 3 to 4 minute continuous running wash over the sample, yielding an estimated 20:1 wash/reagent ratio.

Brigati, D. et al, J. Histotechnology 11: 165-183 (1988) and Unger, E. Brigati, D. et al, et al, J. Histotechnology. 11: 253-258 (1988) describe the Fisher automated work station using capillary gap technology. A coverplate is placed over the slide, forming a capillary gap. Liquid is introduced into the capillary gap by placing the lower edge of the plate-slide pair in a liquid. Liquid is removed by placing the lower edge of the plate-slide pair on a blotter. The system is further described in U.S. Pat. Nos. 4,777,020, 4,798,706 and 4,801,431. The previously known devices are listed in their performance and unable to satisfy the needs for automated, high precision immunohistology.

The foregoing discussion of the prior art derives in large part from U.S. Pat. No. 5,654,200 to Copeland et al., who describe an automated biological processing system comprising a reagent carousel cooperating with a sample support carousel to apply a sequence of preselected reagents to each of the samples with interposed mixing, incubating, and rinsing steps cooperating therewith. This patented automated biological processing system, which is available from Ventana Medical Systems, Inc. of Tucson, Ariz. includes a slide support carousel having a plurality of slide supports thereon and drive means engaging the slide support carousel for consecutively positioning each of a plurality of slide supports in a reagent receiving zone. The reagent carousel has a plurality of reagent container supports thereon and drive means engaging the reagent carousel for rotating this carousel and positioning a preselected reagent container support and associated reagent container in a regent supply zone. The apparatus has a reagent delivery actuator means positioned for engaging a reagent container positioned on a container support in the reagent supply zone and initiating reagent delivery from the reagent container to a slide supported on a slide support in the reagent receiving zone.

FIG. 1, which largely corresponds to FIG. 3 of U.S. Pat. No. 5,654,200 is a partial exploded isometric view of an automated biological processing system, with the cabinet, liquid and air supply tubing and electrical wiring omitted in the drawings for the purposes of clarity.

The apparatus has an upper section 2, intermediate section 4 and lower section 6. In the upper section 2, reagent bottle support carousel 10 is mounted for rotation about its central axis on upper support plate 8. Reagent bottles 12 required for the immuno-histochemical reactions to be conducted during slide treatment cycle are supported by the carousel 10, mounted in reagent bottle receptors 11. These receptors 11 are configured to receive volumetric pump outlet tubes (not shown). The receptors 11 are preferably equally spaced in a circular pattern axially concentric with the carousel axis. The number of receptors 11 provided should be sufficient to accommodate the number of different reagent bottles 12 required for a cycle or series of cycles. The carousel 10 is rotated by the stepper motor 14 and drive belt 16 to a position placing a selected reagent bottle 12 in the reagent delivery position under an air cylinder reagent delivery actuator 18 over a slide to be treated with reagent. Reagent tray motor driver 20 is connected to stepper motor 14.

The intermediate section 4 comprises support plate 22 upon which the slide support carousel 24 is rotatably mounted. The carousel 24 supports slide supports 26. In the intermediate section 4, a stepper motor 48 rotates the slide support carousel 24, engaging drive belt 25 engaging the perimeter of the slide support carousel 24. Splash guard 50 is a wall which surrounds the sides, back and part of the front of the carousel 24, and contains liquid spray and droplets produced in the processing. Splash guard 50 extends upward from the intermediate plate 22 to a position adjacent the upper plate 8, leaving an air flow gap between the upper edge of the splash guard 50 and the underside of the plate 8. Lower section 6 includes slide carousel stepper motor driver 72 and relay 74, power supplies 76 and 78, and control systems all mounted on plate 40.

Referring to FIGS. 2 and 3, slide support 26 comprises a molded plastic base 80 on which is mounted a metal plate 82. An electrical resistance heater shown in phantom at 84 is mounted in direct contact to the underside of metal plate 82. Corner pins 86 locate a specimen carrying glass slide 88 on the surface of metal plate 82. Metal plate 82 has a top surface that is essentially flat and smooth. Flatness and smoothness facilitates glass plate position stability and thermal conduction uniformity.

In practice, water and other fluids employed in the slide processing may spill over the edges of the slides, and work their way under the slides where the fluids may boil, causing the slides to "pop" or dislocate. Moreover, since heater surfaces are not perfectly flat, in order to insure good thermal contact between metal plate 82 and glass slide 88, a thin layer 90 of oil may be applied to the top surface of metal plate 82. However, using oil as an interfacial heating medium, may exacerbate the problem of slide popping or dislocation due to gas formation from water or other fluid getting under the slide, mixing with the oil and then boiling off in an uncontrolled fashion. Dislocation of a slide may cause that slide to set up on a post, thereby compromising the processing of that one slide, or in a worse case scenario result in a domino or train wreck effect where the one dislocated slide hits a neighboring slide causing that slide to dislocate, and so forth.

BRIEF DESCRIPTION OF THE INVENTION

The present invention overcomes the aforesaid and other disadvantages of the prior art, by patterning the slide heater upper surface and/or the glass slide underside surface with ridges or slots, whereby gas bubbles generated by boiling of water trapped between the slide heater and the slide may be channeled, to edges of the slide heater, where the gas may escape or vent without lifting or otherwise dislocating the glass slide.

BRIEF DESCRIPTION OF THE DRAWINGS

Further features and advantages of the present invention will be seen from the following detailed description, taken in conjunction with the accompanying drawings, wherein.

DETAILED DESCRIPTION OF PREFERRED EMBODIMENTS

Figure 1:
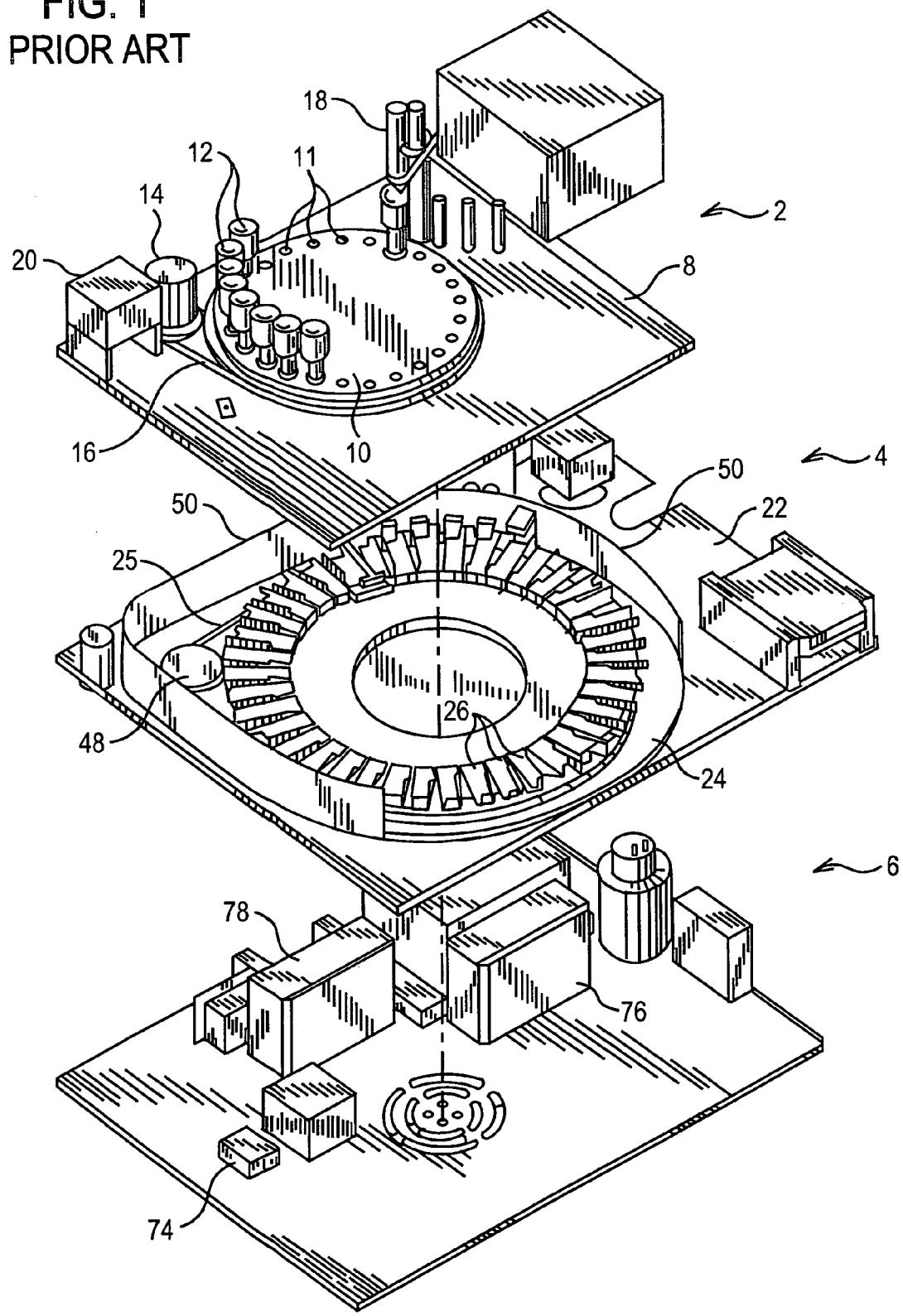
FIG. 1 is a partial exploded isometric view of a prior art automated slide processing apparatus.
Figure 2:
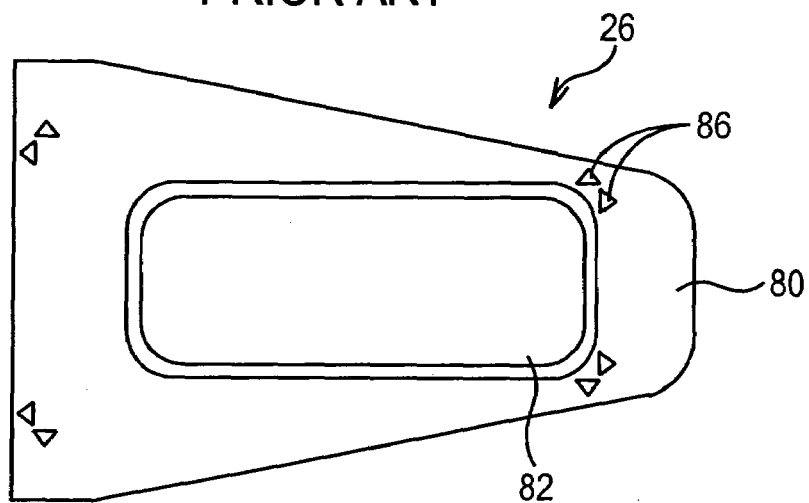
FIG. 2 is a top plan view of a prior art slide support and heater.
Figure 3:
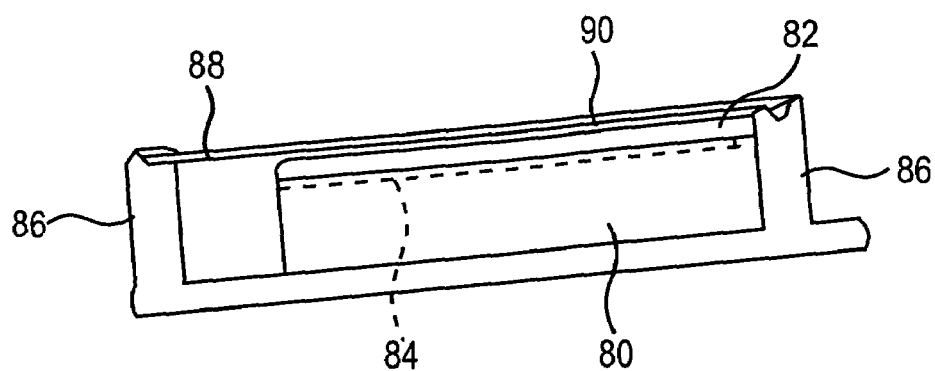
FIG. 3 is a side elevational view of a prior art slide support and heater.

The present invention is based on the discovery that ridges or slots formed on the upper surface of the slide heater and/or on the lower surface of the slides serve to route or channel bubbles formed by the boiling of water or other fluid trapped between the slide heater and slide, to edges of the slide, where the bubbles may vent without dislodging the slide. As mentioned supra, heater surfaces are not perfectly flat. Thus, slight variations in surface heaters may result in a bias or pooling of gas, i.e., steam bubble migration to low areas, and/or in the case of a slide having an interfacial layer or oil, into and through regions of deeper oil. In the case of prior art slide heaters, the migrating gas could pool to a vapor pocket which could "pop" the slide. The present invention takes advantage of the phenomena of gas bubble migration by creating channels for the gas which terminate at open edges of the slide heater. Gas bubbles forming on the surface of the heater migrate to the channels, displace any oil present in the channels, and run to the ends of the channels, where the migrating gas bubbles vent harmlessly from the slide heater edges without dislodging the slide.

An important feature and requirement of any slide heater is to provide substantially uniform heating across a slide since non-uniformity of heating could result in unreliable analytical results. Thus, the general wisdom has been to make heater surfaces and slide surfaces as smooth as possible, i.e., so as to achieve maximum contact or match. Unexpectedly, it has been found that up to about 50% of the slide heater upper surface and/or glass slide may be removed, i.e., by patterning with channels or slots, without adversely affecting thermal conduction uniformity and temperature uniformity distribution across the interface between the slide heater and the glass slide. In other words, provided about at least 50% of the slide heater and glass slide facing surfaces are retained, there is sufficient thermal conduction uniformity between the heater and the slide to mediate slight thermal differences between the low and high parts of the slots or channels resulting in substantially uniform heating of the slide.

The slots or channels may be formed by machining, casting or etching, and should be spaced close enough together so that nucleating gas bubbles do not have to travel too far before reaching a slot or channel. Typically, the slots or channels are spaced about 2 to 5 millimeters on center, preferably about 3 to 4 millimeters. Spacing the slots or channels more than about 10 millimeters apart, on center, may permit gas bubble pooling and thus may not provide sufficient glass slide stability. On the other hand, forming slots or channels closer than about 3 millimeters, on center, may result in removal of a greater percentage of the surface than ideal for uniform thermal conductivity, depending on the width of the slots or channels. Also, placing the slots or channels too close together, and/or forming a large number of narrow slots or channels, adds to initial fabrication costs and may make cleaning more difficult; and, making the channels or slots overly narrow could restrict free venting of gas.

Preferably the slots or channels are similar in size and shape, and run parallel or near parallel to one another, and preferably run from side edge to side edge of the heater. The aspect ratio of the slots or channels per se appears to have little affect on the ability to gather and vent nucleating gas bubbles. Nor does the cross-sectional shape of the slots or channels significantly affect the ability to gather and vent nucleating gas bubbles provided the slots or vents are not overly narrow. As a practical matter, rounded or square edge slots or channels, which could be formed simply by machining, are preferred. Alternatively, the slots or channels can be cast.

Figure 4:
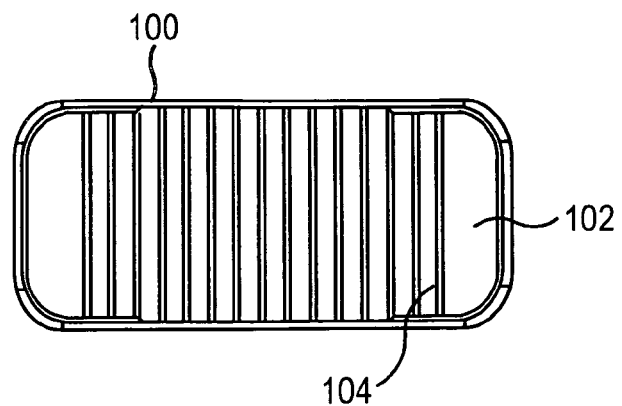
FIG. 4 is a top plan view of a slide support heater made in accordance with a first embodiment of the present invention.
Figure 5:
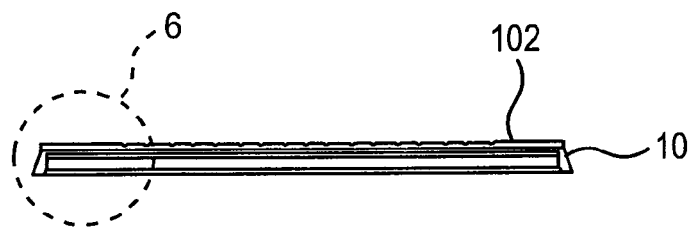
FIG. 5 is a side elevational view, in cross-section, of a slide support heater of FIG. 4.
Figure 6:
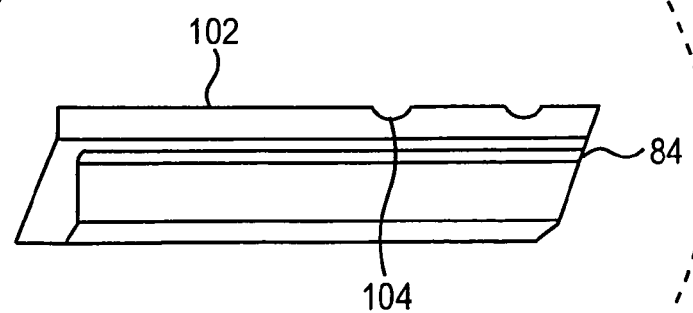
FIG. 6 is an enlarged detail view, in cross-section, of a portion of the slide heater of FIG. 5.

Referring now to FIGS. 4-6, there is shown a first embodiment of slide heater made in accordance with the present invention. (For clarity, details other than the heater surface have been omitted). The heater 100 has an upper surface 102 in which are formed 15 substantially parallel grooves 104. Slots or channels 104 have a rounded bottom of about 0.4 millimeter radius, and run from side to side of the heater 100. The slots or channels 104 are approximately 0.25 millimeter at their deepest point, and are spaced at about 3 millimeters on center.

Figure 7:
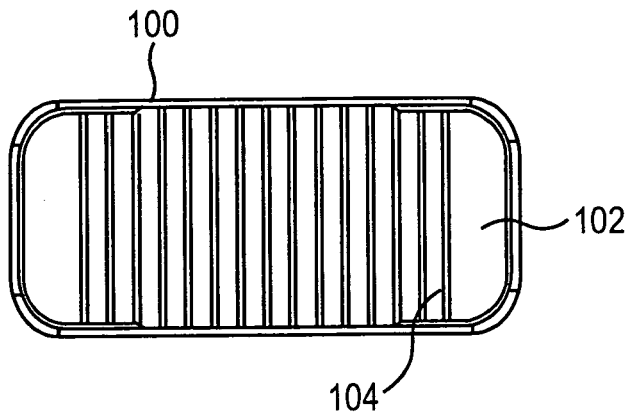
FIG. 7 is a view similar to FIG. 4 showing details of an alternative slide support heater in accordance with the present invention.
Figure 8:
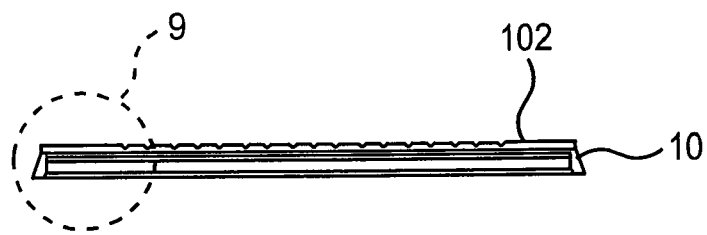
FIG. 8 is a side elevational view of the slide support heater of FIG. 7.
Figure 9:
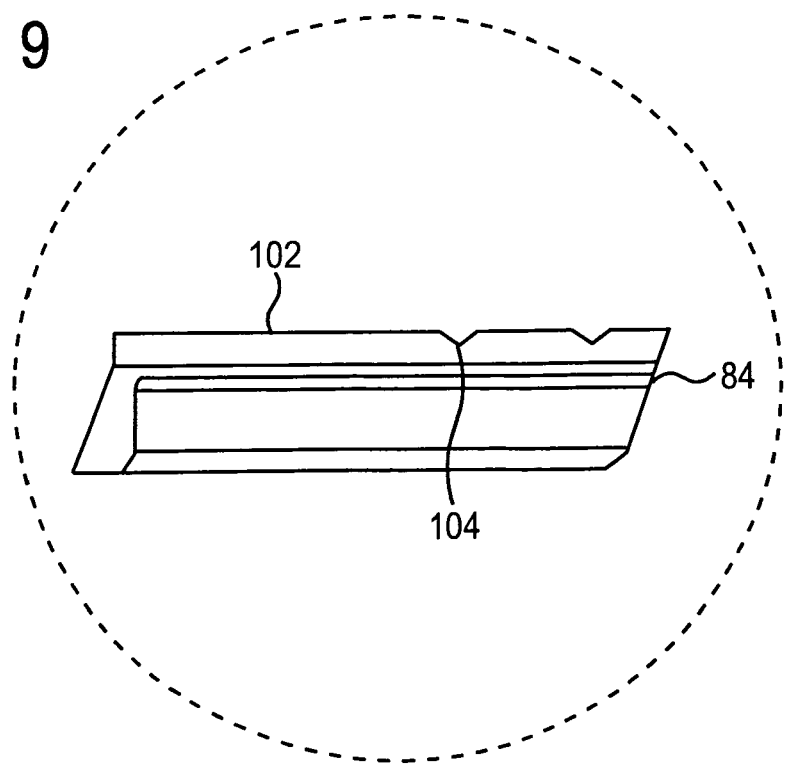
FIG. 9 is an enlarged detail view of the slide support heater of FIG. 8.

Referring to FIGS. 7-9, where there is shown an alternative slide heater made in accordance with the present invention. The FIGS. 7-9 embodiment differs from the embodiment of FIGS. 4-6 in that the slots or channels are "v" shaped.

Figure 10:
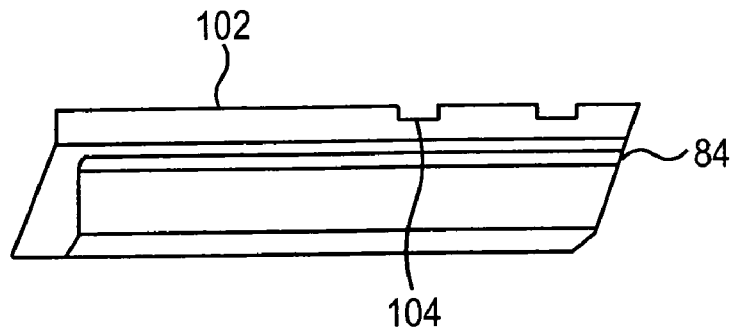
FIGS. 10 and 11 are views, similar to FIG. 9, of yet other embodiments of slide support heaters made in accordance with the present invention.
Figure 11:
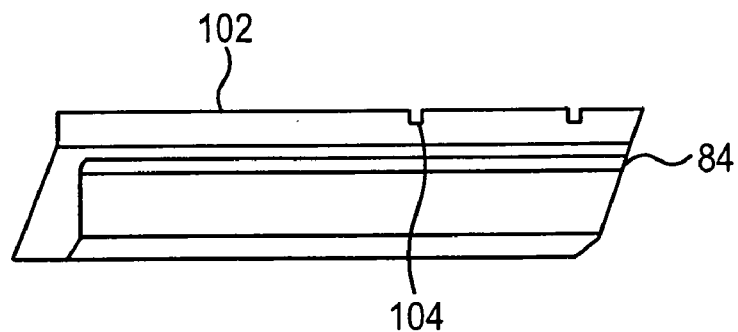

In yet another embodiment illustrated in FIG. 10, the slots or channels are rectilinear in shape, and have a depth-to-width ratio of about 0.2 to 2, preferably about 0.3 to 0.5. FIG. 11 is similar to FIG. 10, in which the slots or channels have a different depth-to-width ratio.

Figure 12:
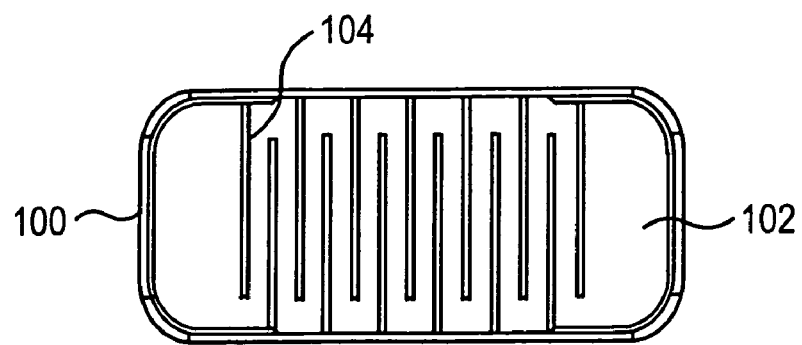
FIGS. 12-14 are views similar to FIG. 4 of yet other embodiments of slide support heaters made in accordance with the present invention.

Various changes may be made in the invention without departing from the spirit and scope thereof. For example, as shown in FIG. 12, the slots or channels may be formed blind at one end.

Figure 13:
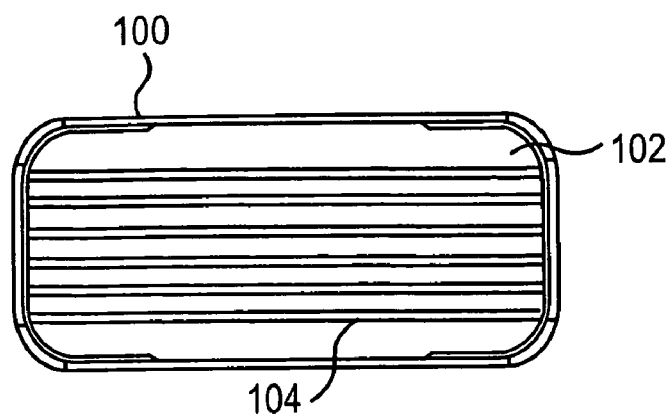
Figure 14:
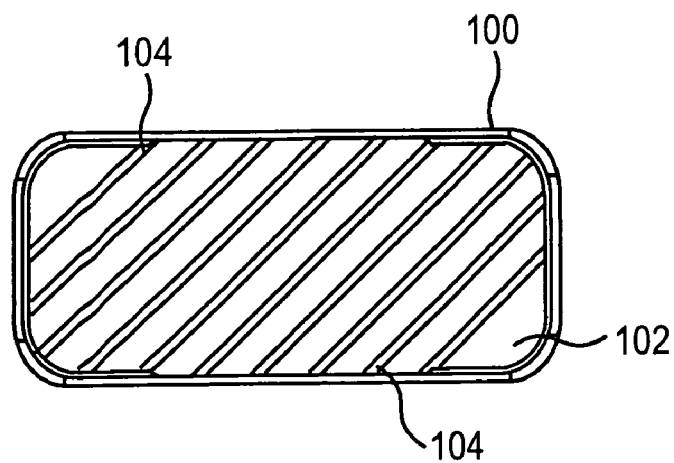
Figure 15:
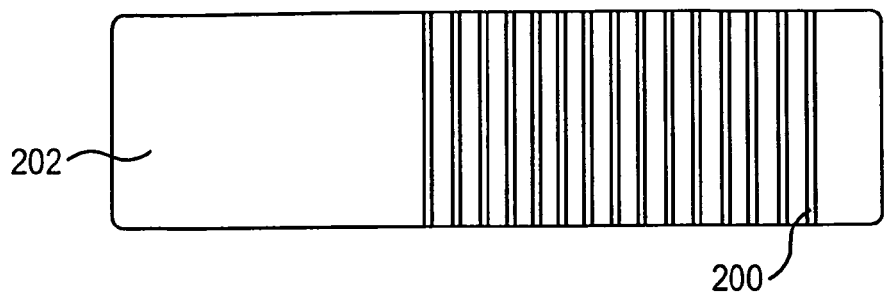
FIGS. 15-17 are views similar to FIGS. 4-6, respectively, of still another alternative of the present invention.
Figure 16:
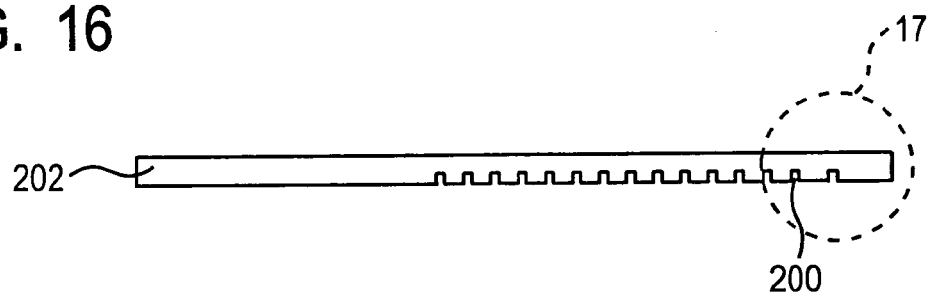
Figure 17:
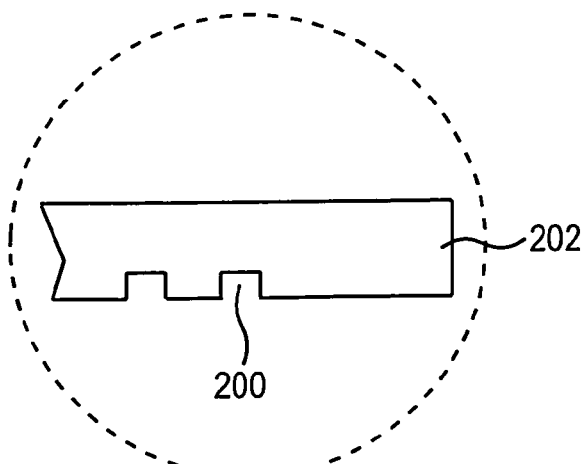
Figure 18:
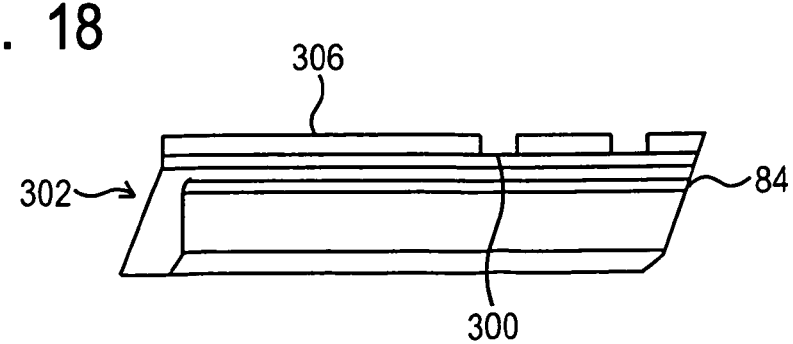
FIGS. 18 and 20 and 19 and 21, are views similar to FIGS. 6 and 17, respectively, of still other alternative of the present invention.
Figure 19:
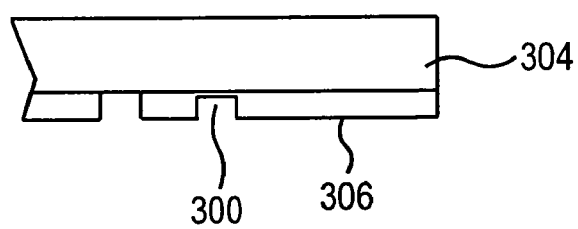
Figure 20:
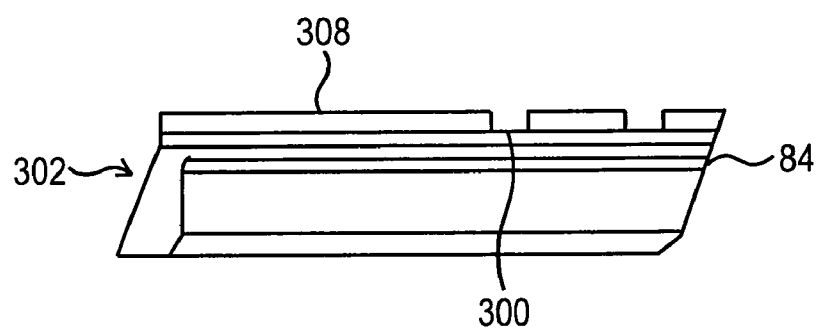
Figure 21:
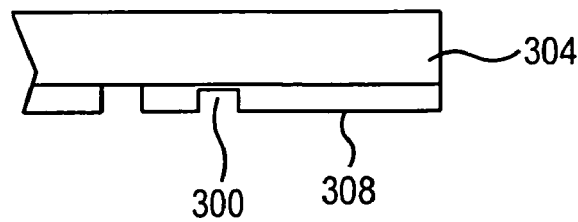

It also may be possible to orient the slots or channels to run the length rather than the width of the heaters (FIG. 13), or at a diagonal (FIG. 14). However, doing so increases the length of the slots or channels, and could result in pooling of gas bubbles in an individual slot or channel, as well as increased transit time to the edges of the slots or channels before the gas could be vented. Accordingly, for optimization purposes, it is preferred that the slots or channels are made as short as possible and run side to side with no interconnections from slot to slot, i.e. the slots should not intersect. In yet another embodiment of the invention, illustrated in FIGS. 15-17, slots or channels 200, similar in arrangement to slots or channels 104, may be provided on the underside of a glass slide 202, and provide similar function.

Yet other changes may be made without departing from the spirit and scope of the invention. For example, instead of machining or casting referring to FIGS. 18-21, slots in channels in the interface surface of the heater or the glass slide, spaced raised regions 300 may be formed on the interface surface of the heater 302 on the glass slide 304 by applying a thermally conductive decal much as a patterned metal foil 306, or by printing with a thermally conductive ink or coating 308 or the like, so as define slots or channels therebetween.

The invention claimed is:

1. In a slide heater for use in a slide processing apparatus in which slides are treated with fluids and heated substantially uniformly across the slide's surface via a thermal conduction transfer interface surface between an upper surface of the slide heater and a slide carried thereon, the improvement wherein said upper surface of the slide heater has a plurality of slots or channels formed therein running to an edge thereof, wherein the slots or channels occupy up to about 50% of the upper surface area of said heater, and have a depth-to-width ratio of about 0.2 to 2, said slots or channels being open at least one end thereof whereby to permit venting of bubbles formed by boiling of fluid as may be trapped between the slide heater and a slide carried thereon without lifting or dislocating the slide.

2. In a slide heater according to claim 1, wherein the slots or channels run from edge to edge.

3. In a slide heater according to claim 1, wherein the slots or channels run parallel to one another.

4. In a slide heater according to claim 1, wherein the slots or channels have a rounded bottom.

5. In a slide heater according to claim 1, wherein the slots or channels are v shaped in cross-section.

6. In a slide heater according to claim 1, wherein the slots or channels are rectilinear in cross-section.

7. In a slide heater according to claim 1, wherein said slots in channels have a depth-to-width ratio of about 0.3 to 0.5.

8. In a slide heater according to claim 1, wherein the slots or channels are blind at one end.

9. In a slide heater according to claim 1, wherein the slots or channels are spaced about 2 to 5 millimeters apart, on center.

10. In a slide heater according to claim 9, wherein the slots or channels are spaced about 3 to 4 millimeters, on center.

11. In a slide heater according to claim 1, wherein the slots or channels are formed by machining.

12. In a slide heater according to claim 1, wherein the slots or channels are formed by casting.

13. In a slide heater according to claim 1, wherein the slots or channels are formed by etching.

14. In a slide heater according to claim 1, where the slots or channels are formed between raised regions on the heater interface upper surface.

15. In a slide heater according to claim 14, wherein the slots or channels are defined between raised regions.

16. In a slide heater according to claim 15, wherein said raised regions are formed by a thermally conductive patterned decal.

17. In a slide heater according to claim 15, wherein said raised regions are defined by a patterned foil.

18. In a slide heater according to claim 15, wherein said raised regions are defined by a thermally conductive ink or coating.

* * * * *